(12) United States Patent
Amari et al.

(10) Patent No.: US 8,097,264 B2
(45) Date of Patent: Jan. 17, 2012

(54) NATURAL EMULSIFYING AGENT

(75) Inventors: Sergio Amari, Paderno D'Adda (IT); Cristina Schubert, Milan (IT)

(73) Assignee: HallStar Italia S.r.l., Milan (IT)

( * ) Notice: Subject to any disclaimer, the term of this patent is extended or adjusted under 35 U.S.C. 154(b) by 1691 days.

(21) Appl. No.: 10/877,989

(22) Filed: Jun. 29, 2004

(65) Prior Publication Data

US 2005/0002882 A1    Jan. 6, 2005

(51) Int. Cl.

| | |
|---|---|
| A61K 8/02 | (2006.01) |
| A61K 8/00 | (2006.01) |
| A61K 8/18 | (2006.01) |
| A61K 36/63 | (2006.01) |
| A61Q 17/04 | (2006.01) |
| A61Q 1/06 | (2006.01) |
| A61Q 5/00 | (2006.01) |
| A61Q 1/10 | (2006.01) |
| A61Q 9/02 | (2006.01) |
| A61Q 19/00 | (2006.01) |

(52) U.S. Cl. ......... 424/401; 424/59; 424/64; 424/70.1; 424/70.7; 424/73; 424/769

(58) Field of Classification Search .......... 424/401, 424/59, 64, 70.1, 70.7, 73, 769
See application file for complete search history.

(56) References Cited

U.S. PATENT DOCUMENTS

| | | | |
|---|---|---|---|
| 4,927,464 A | 5/1990 | Cowie | |
| 5,075,331 A | 12/1991 | Lang et al. | |
| 5,260,336 A * | 11/1993 | Forse et al. | 514/560 |
| 5,314,685 A | 5/1994 | Tyle et al. | |
| 5,502,076 A | 3/1996 | Dixit et al. | |
| 5,653,970 A * | 8/1997 | Vermeer | 424/70.24 |
| 5,968,528 A * | 10/1999 | Deckner et al. | 424/401 |
| 6,140,435 A * | 10/2000 | Zanotti-Russo | 526/238.2 |
| 6,143,307 A | 11/2000 | Maurin | |

FOREIGN PATENT DOCUMENTS

| | | |
|---|---|---|
| FR | 2 377 193 | 8/1978 |
| FR | 2 634 120 | 1/1990 |
| FR | 2 832 057 | 5/2003 |
| WO | WO 94/18292 | 8/1994 |
| WO | WO 00/00174 | 1/2000 |
| WO | WO 0203929 A1 * | 1/2002 |

OTHER PUBLICATIONS

Machine translation of FR 2 832 057.*
R. Celades et al.: "Preparation des esters de polyoxyethyleneglycols par glycolyse" Proceedings of the IVth International Congress on Surface Active Substances, Brussels, Sep. 7-12, 1964, vol. 1, pp. 249-255, XP008026227 *table P.253*.

* cited by examiner

*Primary Examiner* — Sreeni Padmanabhan
*Assistant Examiner* — Jody Karol
(74) *Attorney, Agent, or Firm* — Kenyon & Kenyon LLP

(57) ABSTRACT

A natural emulsifying or coemulsifying agent is formed from fatty acids of olive oil emulsified with 5 to 8 mol ethoxylated cetyl stearyl alcohol. This natural emulsifier is particularly suited for applications in the field of cosmetics, particularly in cosmetic creams, to produce products exhibiting a pleasant silk touch, with hydrating properties and good smoothness.

25 Claims, No Drawings

NATURAL EMULSIFYING AGENT

FIELD OF THE INVENTION

The present invention refers to a natural emulsifying agent, exhibiting a pleasant silk touch, good hydrating properties and a good smoothness, particularly for the use in the cosmetic field.

BACKGROUND OF THE INVENTION

Most cosmetic products include simultaneously water soluble and oil soluble compounds, which should be mixed together and which cannot separate into two or more phases, since otherwise the action is no longer so effective as in mixed form. Therefore, they should form an emulsion. The formation of an emulsion often requires the use of an emulsifier.

Up to now a lot of synthetic emulsifiers have been used. Among them, emulsifier based on alcohols, fat acids or ethoxylated esters are usually employed. The use of such substances can be harmful for human skin and their viscosity is sometimes too high. The advantage of using a functional ingredient derived from olive oil is due to the high similarity of fatty acids contained in olive oil with the acids in the skin. This is the reason why the product has a high compliance with the human skin, good absorption and a light skin feeling.

A few natural emulsifiers have been tested, but either they are not so effective as the synthetic ones or they should be used in large amounts.

SUMMARY OF THE INVENTION

The above problems can be overcome by means of this invention, concerning a natural emulsifying agent, characterised in that it consists of fat acids of olive oil esterified with 5 to 8 (preferably 6) mol ethoxylated cetyl stearyl alcohol.

Particularly, this invention refers to the use of such emulsifying agent in the cosmetic field.

DETAILED DESCRIPTION OF THE INVENTION

This invention refers to a natural emulsifier, consisting of fat acids of olive oil esterified with 5 to 8 mol ethoxylated cetyl stearyl alcohol. Particularly effective is an emulsifier wherein the said fat acids are esterified with 6 mol ethoxylated cetyl stearyl alcohol. The inventive emulsifier can be used in emulsified, hyperfluid, fluid and consistent oil/water systems and it can be used in emulsified and non-emulsified products for use on skin, hair and mucous membranes.

According to this invention, the emulsifying agent can be used as coemulsifying agent in silicone containing mixtures, in water/oil mixtures and/or in water/oil/water mixtures.

It could be used in any kind of cosmetics, particularly in cosmetic creams, creams for hair, creams for hand, foot and nail care, sun protection products, after sun products, professional cosmetic and aesthetics products, dyes, zinc oxide creams, shave creams, liquid and solid soaps and hair-removing creams.

The emulsifying agent according to this invention can also be used in make-ups, like compact powders, sticks, lip-sticks, mascara, eyeliner, fluid and creamy foundations. It can be used also for shampoos and masks for hair.

According to a particular aspect of the present invention, it can be used as consistent wax in anhydrous products. Examples of such products are lipid gels, lipsticks and masks for hair. Moreover, it can be used as wax for modifying the smoothness or as an emollient.

The preparation of the emulsifying agent according to this invention starts from pure olive oil esterified with 6 mol ethoxylated cetylstearilic acid according to the conventional methods of organic chemistry.

The obtained ester is able to perform a gel network into water, which stabilises the emulsion, provides a fast absorption effect and hinders the skin water loss.

It can be added in an amount between 0.5 and 8%, with 0-30% of a lipid phase, having different polarity values.

Under 0.5%, the emulsifying agent has no effect, whilst an addition over 8% is unuseful, since no improvement is noticed.

A low viscosity emulsion can be particularly appreciated, containing 0.5 to 1% of the emulsifying agent of this invention (hyperfluid systems). Also particularly preferred is a 5-30% lipid phase, containing 2 to 3% of the emulsifying agent (very fluid structures). Particularly preferred is also an emulsion containing 3 to 5% of the emulsifying agent of the invention (consistent emulsion).

The emulsifying agent of the present invention can be used as unique emulsifying, with no gelling in the aqueous phase, up to 8%.

The use as unique emulsifying agent is very simple: the fat phase is molten at 70-75° C.; the aqueous phase is mixed at 70° C.; under stirring and homogenisation, the fat phase is added to the aqueous one, then it is homogenised for 5-10 minutes, then it is cooled under stirring.

This invention is now described more in depth by the following examples, which are by no means intended to limit the invention.

Example 1

A day cream was prepared by mixing the following phases:

| PHASE A: | Emulsifying agent according to the invention: | 5.0% |
|---|---|---|
| | Octyldodecanol: | 5.0% |
| | Isodecyl neopentanoate: | 5.0% |
| | Dimethicone: | 2.0% |
| | Miristyl Miristate: | 2.0% |
| | Cetearyl alcohol: | 2.0% |
| PHASE B: | Demineralised water | bal. to 100% |
| | Carbomer: | 0.2% |
| | Propylene glycol: | 3.0% |
| | Preservatives: | as needed |
| | 30% NaOH: | as needed |
| PHASE C: | Perfume: | as needed. |

First of all phase A and B were prepared, then they were both heated up to 60° C. The phases were mixed and homogenised, at the same temperature, then they were cooled down quickly under stirring. Subsequently, phase C was added.

The obtained mixture was odourless, white, in even chips and exhibited a drop point at 63° C. After stabilisation at 40° C., the mixture did not exhibit any change in properties after two months.

Example 2

A consistent cream was prepared, containing the following components:

| PHASE A: | Emulsifying agent according to the invention: | 5.0% |
|---|---|---|
| | GMS/PEG 100 stearate: | 2.0% |
| | Cetyl palmitate: | 2.0% |

-continued

|         |                    |                    |
|---------|--------------------|--------------------|
|         | Cetearyl alcohol:  | 1.0%               |
|         | Oil of sweet almond: | 5.0%             |
|         | Isononyl nonanoate: | 10.0%             |
|         | Dimethicone:       | 2.8%               |
|         | Refined olive oil: | 3.0%               |
| PHASE B: | Demineralised water: | Balance to 100% |
|         | Glycerin:          | 3.0%               |
|         | Carbomer Ultrez 10: | 0.3%              |
|         | Panthenol:         | 0.5%               |
|         | Aloe:              | 0.2%               |
| PHASE C: | 30% NaOH:         | to pH 5.5 ± 0.3    |
| PHASE D: | EUROL BT ™        | 0.3%               |
| PHASE E: | Perfume:           | as needed          |
|         | Preservatives:     | as needed          |

Phases A and B were heated up to 70-75° C.; subsequently phase A was added to phase B and they were homogenised for 5 minutes. The mixture was cooled down slowly under stirring and phases C, D and E were added.

Example 3

A Light cream was prepared, which contained the following phases:

|          |                                          |                 |
|----------|------------------------------------------|-----------------|
| PHASE A: | Emulsifying agent according to the invention: | 2.0%       |
|          | Jojoba oil:                              | 6.0%            |
| PHASE B: | Demineralised water:                     | balance to 100% |
|          | Xanthan gum:                             | 0.2%            |
|          | Hydroxypropyl starch phosphate:          | 2.0%            |
| PHASE C: | Preservatives:                           | as needed       |
|          | perfume                                  | as needed       |

Phase A and phase B were prepared separately and heated up to 70° C. They were mixed and homogenised at 70° C. for 5 minutes. Subsequently, the obtained compound was cooled down quickly under stirring and phase C was added.

Example 4

A natural emulsion was prepared, containing the following phases:

|          |                                          |                 |
|----------|------------------------------------------|-----------------|
| PHASE A: | Emulsifying agent according to the invention: | 5.0%       |
|          | oil of peanuts:                          | 4.0%            |
|          | oil of grape seeds:                      | 3.0%            |
|          | oil of corn:                             | 2.0%            |
|          | oil of jojoba:                           | 5.0%            |
|          | tocopherol acetate:                      | 0.5%            |
|          | ceramide III:                            | 0.3%            |
| PHASE B: | demineralised water:                     | balance to 100% |
|          | hydroxypropyl starch phosphate:          | 2.0%            |
|          | xanthan gum:                             | 0.4%            |
|          | glycerin:                                | 3.0%            |
|          | aloe 10:1:                               | 0.3%            |
| PHASE C: | Preservatives:                           | as needed       |
|          | bisabolol:                               | 0.2%            |
|          | perfume:                                 | as needed       |

Phases A and B were separately prepared and heated up to 70° C. They were mixed and homogenised for 5 minutes, the they were cooled down quickly under stirring. Finally, phase C was added.

Example 5

A fluid emulsion was prepared, which contained the following components:

|          |                                          |                 |
|----------|------------------------------------------|-----------------|
| PHASE A: | Emulsifying agent according to the invention: | 2.0%       |
|          | isononyl isononanoate:                   | 6.0%            |
| PHASE B: | Demineralised water:                     | balance to 100% |
|          | xanthan gum:                             | 0.4%            |
| PHASE C: | Preservatives:                           | as needed       |
|          | perfume:                                 | as needed       |

Phases A and B were separately prepared and heated up to 70° C. They were mixed and homogenised for 5 minutes, then cooled down quickly under stirring. Finally, phase C was added.

Example 6

An oil-free cream was prepared, which contained the following components:

|          |                                          |                 |
|----------|------------------------------------------|-----------------|
| PHASE A: | Emulsifying agent according to the invention: | 2.0%       |
|          | OLIVEM 900 ™                             | 0.5%            |
|          | Sorbitan palmitate                       | 0.4%            |
|          | Cetyl palmitate                          | 0.9%            |
|          | Cetyl alcohol                            | 0.2%            |
|          | Isononyl isononanoate                    | 6.0%            |
| PHASE B: | Demineralised water:                     | balance to 100% |
|          | Xanthan gum:                             | 0.45            |
| PHASE C: | Preservatives:                           | as needed       |
|          | Perfume:                                 | as needed       |

Phases A and B were separately prepared and heated up to 70° C. They were mixed and homogenised for 5 minutes, then cooled down quickly under stirring. Finally, phase C was added.

Example 7

A hydrating lotion was prepared, which contained the following components:

|          |                                          |                 |
|----------|------------------------------------------|-----------------|
| PHASE A: | Emulsifying agent according to the invention: | 4.0%       |
|          | Oil of jojoba:                           | 5.0%            |
|          | Oil of wheat germ:                       | 10.0%           |
| PHASE B: | Demineralised water:                     | balance to 100% |
|          | Aqua algae:                              | 10.0%           |
|          | Xanthan gum:                             | 0.3%            |
| PHASE C: | Preservatives:                           | as needed       |
|          | Perfume:                                 | as needed       |

Phases A and B were separately prepared and heated up to 70° C. They were mixed and homogenised for 5 minutes, then cooled down quickly under stirring. Finally, phase C was added.

Example 8

An anti-age fluid was prepared, which contained the following components:

| PHASE A: | Emulsifying agent according to the invention: | 3.0% |
|---|---|---|
| | Isopropyl miristate: | 4.0% |
| | Cyclomethicone: | 1.0% |
| | Shea butter: | 1.0% |
| | Dimethicone: | 1.5% |
| | Mineral oil: | 12.0% |
| | Ceramide III: | 0.5% |
| | Tocopheryl acetate: | 0.5% |
| PHASE B: | Demineralised water: | balance to 100% |
| | Glycerin: | 3.0% |
| | Carbomer 2050: | 0.5% |
| | NaOH: | as needed |
| PHASE C: | Eurol BT ™: | 0.25% |
| | Soja extract: | 2.0% |
| | Preservatives: | as needed |
| | Perfume: | as needed |

Phases A and B were separately prepared and heated up to 70° C. They were mixed and homogenised for 5 minutes, then cooled down quickly under stirring. Finally, phase C was added.

Example 9

A hair-care cream was prepared, which contained the following components:

| PHASE A: | Emulsifying agent according to the invention: | 5.0% |
|---|---|---|
| PHASE B: | Demineralised water: | balance to 100% |
| | aloe: | 0.2% |
| | citric acid: | to pH 4.5 |
| | hydroxypropyl guar: | 0.3% |
| | panthenol: | 0.5% |
| | hydroxyethylcellulose: | 0.6% |
| PHASE C: | DC 2-8177 ™: | 2.0% |
| PHASE D: | preservatives: | as needed |

Phases A and B were separately prepared, dispersed in hot water and heated up to 70° C. They were mixed and homogenised for 5 minutes, then cooled down quickly under stirring. Finally, phases C and D were added.

Example 10

A hyper-fluid system was prepared, which contained the following components:

| PHASE A: | Emulsifying agent according to the invention: | 2.0% |
|---|---|---|
| | Oil of sweet almonds: | 5.0% |
| PHASE B: | Demineralised water: | balance to 100% |
| | Glycerin: | 5.0% |
| | Microcrystalline cellulose, carboxy Methylcellulose: | 1.5% |
| | Xanthan gum: | 0.15% |
| PHASE C: | Preservative | as needed |

Phase A and phase B were prepared separately and heated at 75-80° C. Phase A was slowly added to phase B. The mixture was homogeinised for a couple of minutes. The compound was cooled under slow stirring to 30-35° C. and phase C was added.

The invention claimed is:

1. A natural emulsifier formed by a process comprising esterifying fatty acids in olive oil with 5 to 8 mole ethoxylated cetyl stearyl alcohol, wherein the 5 to 8 mole is the cetyl stearyl alcohol degree of ethoxylation, and wherein the starting material being subjected to esterification is olive oil.

2. The natural emulsifier as in claim 1, wherein the fatty acids in the olive oil are esterified with 6 mole ethoxylated cetyl stearyl alcohol, and wherein the 6 mole is the degree of ethoxylation of the cetyl stearyl alcohol.

3. A process for the preparation of an emulsifier according to claim 1, wherein said process comprises reacting pure olive oil with 6 mole ethoxylated cetyl stearyl alcohol to obtain an ester product, the 5 to 8 mole being the degree of ethoxylation of the cetyl stearyl alcohol.

4. A day cream comprising:

| PHASE A: | Emulsifying agent according to claim 1: | 5.0% |
|---|---|---|
| | Octyldodecanol: | 5.0% |
| | Isodecyl neopentanoate: | 5.0% |
| | Dimethicone: | 2.0% |
| | Miristyl Miristate: | 2.0% |
| | Cetearyl alcohol: | 2.0% |
| PHASE B: | Demineralised water | bal. to 100% |
| | Carbomer: | 0.2% |
| | Propylene glycol: | 3.0% |
| | Preservatives: | as needed |
| | 30% NaOH: | as needed |
| PHASE C: | Perfume: | as needed. |

5. A consistent cream, comprising:

| PHASE A: | Emulsifying agent according to claim 1: | 5.0% |
|---|---|---|
| | GMS/PEG 100 stearate: | 2.0% |
| | Cetyl palmitate: | 2.0% |
| | Cetearyl alcohol: | 1.0% |
| | Oil of sweet almond: | 5.0% |
| | Isonorryl nonanoate: | 10.0% |
| | Dimethicone: | 2.8% |
| | Refined olive oil: | 3.0% |
| PHASE B: | Demineralised water: | Balance to 100% |
| | Glycerin: | 3.0% |
| | Carbomer Ultrez 10: | 0.3% |
| | Panthenol: | 0.5% |
| | Aloe: | 0.2% |
| PHASE C: | 30% NaOH: | to pH 5.5 ± 0.3 |
| PHASE D: | EUROL BT ™ | 0.3% |
| PHASE E: | Perfume: | as needed |
| | Preservatives: | as needed. |

6. A light cream, comprising:

| PHASE A: | Emulsifying agent according to claim 1: | 2.0% |
|---|---|---|
| | Jojoba oil: | 6.0% |
| PHASE B: | Demineralised water: | balance to 100% |
| | Xanthan gum: | 0.2% |
| | Hydroxypropyl starch phosphate: | 2.0% |
| PHASE C: | Preservatives: | as needed |
| | perfume | as needed. |

7. A natural emulsion, comprising:

| PHASE A: | Emulsifying agent according to claim 1: | 5.0% |
|---|---|---|
| | oil of peanuts: | 4.0% |
| | oil of grape seeds: | 3.0% |

-continued

|         |                              |                 |
|---------|------------------------------|-----------------|
|         | oil of corn:                 | 2.0%            |
|         | oil of jojoba:               | 5.0%            |
|         | tocopherol acetate:          | 0.5%            |
|         | ceramide III:                | 0.3%            |
| PHASE B:| demineralised water:         | balance to 100% |
|         | hydroxypropyl starch phosphate: | 2.0%         |
|         | xanthan gum:                 | 0.4%            |
|         | glycerin:                    | 3.0%            |
|         | aloe:                        | 0.3%            |
| PHASE C:| Preservatives:               | as needed       |
|         | bisabolol:                   | 0.2%            |
|         | perfume:                     | as needed.      |

8. A fluid emulsion, comprising:

|         |                                      |                 |
|---------|--------------------------------------|-----------------|
| PHASE A:| Emulsifying agent according to claim 1: | 2.0%         |
|         | isononyl isononanoate:               | 6.0%            |
| PHASE B:| Demineralised water:                 | balance to 100% |
|         | xanthan gum:                         | 0.4%            |
| PHASE C:| Preservatives:                       | as needed       |
|         | perfume:                             | as needed.      |

9. An oil-free cream, comprising:

|         |                                      |                 |
|---------|--------------------------------------|-----------------|
| PHASE A:| Emulsifying agent according to claim 1: | 2.0%         |
|         | OLIVEM 900 ™                         | 0.5%            |
|         | Sorbitan palmitate                   | 0.4%            |
|         | Cetyl palmitate                      | 0.9%            |
|         | Cetyl alcohol                        | 0.2%            |
|         | Isononyl isononanoate                | 6.0%            |
| PHASE B:| Demineralised water:                 | balance to 100% |
|         | Xanthan gum:                         | 0.45%           |
| PHASE C:| Preservatives:                       | as needed       |
|         | Perfume:                             | as needed.      |

10. A hydrating lotion, comprising:

|         |                                      |                 |
|---------|--------------------------------------|-----------------|
| PHASE A:| Emulsifying agent according to claim 1: | 4.0%         |
|         | Oil of jojoba:                       | 5.0%            |
|         | Oil of wheat germ:                   | 10.0%           |
| PHASE B:| Demineralised water:                 | balance to 100% |
|         | Aqua algae:                          | 10.0%           |
|         | Xanthan gum:                         | 0.3%            |
| PHASE C:| Preservatives:                       | as needed       |
|         | Perfume:                             | as needed.      |

11. An anti-age fluid, comprising:

|         |                                      |                 |
|---------|--------------------------------------|-----------------|
| PHASE A:| Emulsifying agent according to claim 1: | 3.0%         |
|         | Isopropyl miristate:                 | 4.0%            |
|         | Cyclomethicone:                      | 1.0%            |
|         | Shea butter:                         | 1.0%            |
|         | Dimethicone:                         | 1.5%            |
|         | Mineral oil:                         | 12.0%           |
|         | Ceramide III:                        | 0.5%            |
|         | Tocopheryl acetate:                  | 0.5%            |
| PHASE B:| Demineralised water:                 | balance to 100% |
|         | Glycerin:                            | 3.0%            |
|         | Carbomer 2050:                       | 0.5%            |
|         | NaOH:                                | as needed       |
| PHASE C:| EUROL BT ™:                          |                 |
|         | Soja extract:                        | 2.0%            |
|         | Preservatives:                       | as needed       |
|         | Perfume:                             | as needed.      |

12. A hair-care cream, comprising:

|         |                                      |                 |
|---------|--------------------------------------|-----------------|
| PHASE A:| Emulsifying agent according to claim 1: | 5.0%         |
| PHASE B:| Demineralised water:                 | balance to 100% |
|         | aloe:                                | 0.2%            |
|         | citric acid:                         | to pH 4.5       |
|         | hydroxypropyl guar:                  | 0.3%            |
|         | panthenol:                           | 0.5%            |
|         | hydroxyethylcellulose:               | 0.6%            |
| PHASE C:| DC 2-8177 ™:                         | 2.0%            |
| PHASE D:| preservatives:                       | as needed.      |

13. A hyper-fluid system comprising:

|         |                                      |                 |
|---------|--------------------------------------|-----------------|
| PHASE A:| Emulsifying agent according to claim 1: | 2.0%         |
|         | Oil of sweet almonds:                | 5.0%            |
| PHASE B:| Demineralised water:                 | balance to 100% |
|         | Glycerin:                            | 5.0%            |
|         | Microcrystalline cellulose, carboxy Methylcellulose: | 1.5% |
|         | Xanthan gum:                         | 0.15%.          |

14. The natural emulsifier according to claim 1, wherein the natural emulsifier consists of olive oil, wherein the fatty acids in the olive oil are esterified with 5 to 8 mole ethoxylated cetyl stearyl alcohol.

15. The natural emulsifier according to claim 14, consisting of olive oil, wherein the fatty acids in the olive oil are esterified with 6 mole ethoxylated cetyl stearyl alcohol.

16. A method for preparing a cosmetic, comprising adding the emulsifier according to claim 1 to said cosmetic.

17. A method for preparing a hyperfluid, fluid, or consistent oil/water system comprising adding the emulsifier according to claim 1 to said hyperfluid, fluid, or consistent oil/water system.

18. A method for treating skin, hair, or mucous membrane, comprising applying to said skin, hair, or mucous membrane an effective amount of the emulsifier according to claim 1.

19. The method according to claim 16, wherein the emulsifier is added as a coemulsifying agent in a silicone containing, water/oil, and/or water/oil/water mixture.

20. A method for preparing a cosmetic cream, cream for hair, cream for hand, foot care product, nail care product, sun protection product, after sun product, cosmetic product, aesthetics product, dye, zinc oxide cream, shaving cream, liquid soap, solid soap, or hair-removing cream, comprising adding the emulsifier according to claim 1 to said cosmetic cream, cream for hair, cream for hand, foot care product, nail care product, sun protection product, after sun product, cosmetic product, aesthetics product, dye, zinc oxidecream, shaving cream, liquid soap, solid soap and hair-removing cream.

21. A method for preparing make-up, compact powders, sticks, lip-sticks, mascara, eyeliner, fluid, creamy foundations shampoos, or masks for hair, comprising adding the emulsifier according to claim 1 to said make-up, compact powders, sticks, lip-sticks, mascara, eyeliner, fluid, creamy foundations shampoos, or masks for hair.

22. A method for preparing a consistent wax in an anhydrous product, comprising adding the emulsifier according to claim 1 as consistent wax in an anhydrous product.

23. A method for preparing a lipid gel, lipstick, mask for hair, wax for modifying the smoothness, or emollient, comprising adding the emulsifier according to claim 1 to said lipid gel, lipstick, mask for hair, wax for modifying the smoothness, or emollient.

24. A process for the preparation of an emulsifier according to claim 14, comprising reacting pure olive oil with 6 mole ethoxylated cetylstearilic to obtain an ester product.

25. The method according to claim 16, wherein the emulsifier is added in an amount between 0.5 and 8%, with 0-30% of a lipid phase.

* * * * *

UNITED STATES PATENT AND TRADEMARK OFFICE
CERTIFICATE OF CORRECTION

PATENT NO. : 8,097,264 B2
APPLICATION NO. : 10/877989
DATED : January 17, 2012
INVENTOR(S) : Sergio Amari et al.

It is certified that error appears in the above-identified patent and that said Letters Patent is hereby corrected as shown below:

On the Title page, please add item (30) Foreign Application Priority Data

July 1, 2003 (EP) 03425437.5

In the Specifications

Column 1, line 4, add "cross-references to related application:

This application claims foreign priority benefits under 35 U.S.C. § 119 to European Patent Application No. 03425437.5, filed on July 1, 2003, which is hereby incorporated by reference in its entirety."

Column 1, line 19, change "fat" to -- fatty --;

Column 2, line 3, change "cetylstearilic acid" to -- cetyl stearyl alcohol --;

Column 8, line 63-64, change "foundations shampoos" to -- foundations, shampoos --;

Column 8, line 67, change "foundations shampoos" to -- foundations, shampoos --;

Column 10, line 3, change "cetylstearilic" to -- cetyl stearyl alcohol --;

Signed and Sealed this
Ninth Day of April, 2013

Teresa Stanek Rea
*Acting Director of the United States Patent and Trademark Office*